US012583879B2

(12) United States Patent
Qin et al.

(10) Patent No.: US 12,583,879 B2
(45) Date of Patent: Mar. 24, 2026

(54) METHOD FOR SYNTHESIZING C-NUCLEOSIDE COMPOUND

(71) Applicants: SICHUAN UNIVERSITY, Chengdu (CN); ACADEMY OF MILITARY MEDICAL SCIENCES, Beijing (CN); CHENGDU AUPONE PHARMACEUTICAL CO., LTD, Chengdu (CN)

(72) Inventors: Yong Qin, Chengdu (CN); Wu Zhong, Beijing (CN); Fei Xue, Chengdu (CN); Xiaoyu Liu, Chengdu (CN); Yu Wang, Chengdu (CN); Xiaohan Zhou, Chengdu (CN); Bo Liu, Chengdu (CN); Ke Wang, Chengdu (CN); Likai Yang, Chengdu (CN); Ruijie Zhou, Chengdu (CN); Yaxin Xiao, Chengdu (CN); Fanglin Xue, Chengdu (CN); Minjie Zhang, Chengdu (CN); Hao Song, Chengdu (CN); Zhibing Zheng, Beijing (CN); Song Li, Beijing (CN)

(73) Assignees: SICHUAN UNIVERSITY, Chengdu (CN); ACADEMY OF MILITARY MEDICAL SCIENCES, Beijing (CN); CHENGDU AUPONE PHARMACEUTICAL CO., LTD, Chengdu (CN)

( * ) Notice: Subject to any disclaimer, the term of this patent is extended or adjusted under 35 U.S.C. 154(b) by 561 days.

(21) Appl. No.: 18/016,172

(22) PCT Filed: Jul. 15, 2021

(86) PCT No.: PCT/CN2021/106520
§ 371 (c)(1),
(2) Date: Jan. 13, 2023

(87) PCT Pub. No.: WO2022/012630
PCT Pub. Date: Jan. 20, 2022

(65) Prior Publication Data

US 2023/0219990 A1 Jul. 13, 2023

(30) Foreign Application Priority Data

Jul. 17, 2020 (CN) ........................ 202010692306.3

(51) Int. Cl.
*C07H 1/00* (2006.01)
*C07F 7/10* (2006.01)

(52) U.S. Cl.
CPC *C07H 1/00* (2013.01); *C07F 7/10* (2013.01)

(58) Field of Classification Search
CPC ................................. C07H 1/00; C07H 15/18
See application file for complete search history.

(56) References Cited

FOREIGN PATENT DOCUMENTS

| | | | |
|---|---|---|---|
| CN | 1950362 | A | 4/2007 |
| CN | 103153314 | A | 6/2013 |
| CN | 105899216 | A | 8/2016 |
| CN | 109748921 | A | 5/2019 |
| CN | 111205327 | A | 5/2020 |
| CN | 111233869 | A | 6/2020 |
| CN | 111793101 | A | 10/2020 |
| JP | 2015-535853 | A | 12/2015 |
| JP | 2017-502925 | A | 1/2017 |
| WO | 2005095385 | A1 | 10/2005 |
| WO | 2012037038 | A1 | 3/2012 |
| WO | 2014035140 | A2 | 3/2014 |
| WO | 2014042433 | A2 | 3/2014 |
| WO | 2014/058801 | A1 | 4/2014 |
| WO | 2015069939 | A1 | 5/2015 |
| WO | 2017/027646 | A1 | 2/2017 |
| WO | 2019/053696 | A1 | 3/2019 |

OTHER PUBLICATIONS

Wuts et al., Greene's Protective Groups in Organic Synthesis, 2007, 4th ed., John Wiley & Sons, p. 165-221 and 847. (Year: 2007).*
Cho et al., "Discovery of the First C-Nucleoside HCV Polymerase Inhibitor (GS-6620) with Demonstrated Antiviral Response in HCV Infected Patients", Journal of Medicinal Chemistry, 57:1812-1825 (2014).
Cho et al., "Synthesis and antiviral activity of a series of 1'-substituted 4-aza-7,9-dideazaadenosine C-nucleosides", Bioorganic & Medicinal Chemistry Letters, 22:2705-2707 (2012).

(Continued)

*Primary Examiner* — Jonathan S Lau
(74) *Attorney, Agent, or Firm* — Leason Ellis LLP; James F. Haley, Jr.; Kendra V. Johnson

(57) ABSTRACT

Disclosed is a method for preparing a C-nucleoside compound represented by Formula (III) or salt thereof. The present method has a high reaction yield, is simple to operate, uses a single metal reagent, has stable reaction temperature conditions, does not require frequent changes to the reaction system during the operation process, is suitable for scale-up synthesis, is suitable for large-scale production of Remdesivir, and has low costs.

III

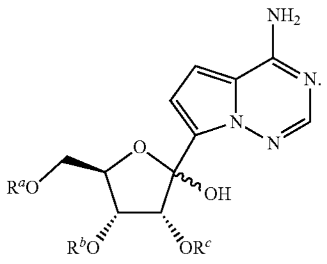

18 Claims, No Drawings

(56) References Cited

OTHER PUBLICATIONS

Cho et al., "Synthesis and characterization of 2'-C-Me branched-C-nucleosides as HCV polymerase inhibitors", Bioorganic & Medicinal Chemistry Letters, 22:4127-4132 (2012).

Djuric et al., "Silicon in Synthesis: Stabase Adducts—A New Primary Amine Protecting Group: Alkylation of Ethyl Glycinate", 22:1787-1790 (1981).

Fen et al., "Synthesis of Remdesivir", China Pharmaceuticals, 29:1006-4931 (2020), (4 pages).

Hildbrand et al., "5-Substituted 2-Aminopyridine C-Nucleosides as Protonated Cytidine Equivalents: Increasing Efficiency and Selectivity in DNA Triple-Helix Formation", Journal of American Chemical Society, 119:5499-5511 (1997).

Metobo et al., "Practical synthesis of 1-substituted Tubercidin C-nucleoside analogs", Tetrahedron Letters, 53:484-486 (2012).

Siegel et al., "Discovery and Synthesis of a Phosphoramidate Prodrug of a Pyrrolo[2,1-f ][triazin-4-amino] Adenine C-Nucleoside (GS-5734) for the Treatment of Ebola and Emerging Viruses", Journal of Medicinal Chemistry, 60:1648-1661 (2017).

Xue et al., "Improvement of the C-glycosylation Step for the Synthesis of Remdesivir", Organic Process Research & Development, 24:1772-1777 (2020).

* cited by examiner

METHOD FOR SYNTHESIZING C-NUCLEOSIDE COMPOUND

CROSS-REFERENCE TO RELATED APPLICATIONS

This application is a national stage application under 35 U.S.C. § 371 of International Application No. PCT/CN2021/106520, filed Jul. 15, 2021, which claims the benefit of and priority from Chinese Application No. 202010692306.3, filed on Jul. 17, 2020. The contents and disclosure of each of the foregoing applications are incorporated by reference herein in their entireties.

The present application is based on and claims the benefit of priority from Chinese application No. 202010692306.3, filed on Jul. 17, 2020, the disclosures of which are incorporated herein by reference in its entirety.

TECHNICAL FIELD

The present application relates to the field of pharmaceutical synthesis, specifically to a method for synthesizing a chiral intermediate C-nucleoside compound of Remdesivir.

BACKGROUND ART

Nucleoside analogs have a unique effect on viruses, a variety of small-molecule nucleoside analogs such as favipiravir, brincidofovir and galidesivir have been found to have some antiviral activity in clinical stages. Gilead screened a large number of nucleoside analogs and found that remdesivir had shown good inhibitory activity against Ebola virus, respiratory syncytial virus, coronavirus, Nipah virus and Hendra virus, etc., and also showed high antiviral activity against the coronavirus SARS-CoV-2. Currently, the Phase III clinical trials for the treatment of SARS-CoV-2 virus infection are being carried out in China, Europe and the United States. In the existing reports related to the synthesis of remdesivir, 7-halogenated pyrrolo[2,1-f][1,2,4]triazin-4-amine (1) and its analogs and D-ribonolactone (2) are the starting materials, and the C-nucleoside compound (3) is obtained by addition reaction, then remdesivir is prepared by further derivatization. Due to the difficulty of remdesivir synthesis, further clinical application research of the drug is seriously restricted.

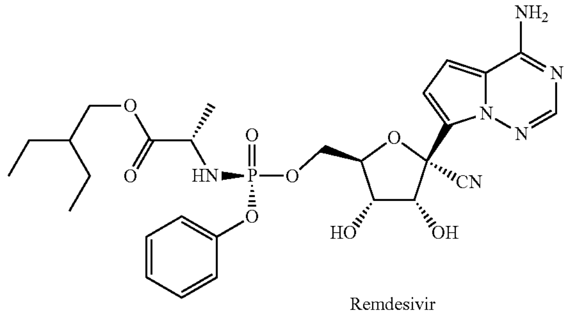

Remdesivir

1

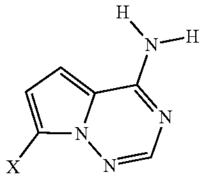

X=halogen

-continued

2

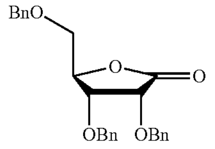

3

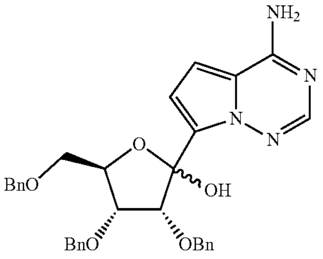

For the synthesis of drugs, the efficient synthesis of starting materials is crucial for reducing the overall cost of drug production. At present, for the key addition reaction in the synthesis of remdesivir, the reported synthetic methods mainly comprise: 7-bromopyrrolo[2,1-f][1,2,4]triazin-4-amine (1a) and D-ribonolactone (2) undergo a metal-halogen exchange reaction through temporarily protecting the amino group in Compound 1a in the presence of trimethylchlorosilane (TMSCl) and n-butyllithium (n-BuLi), then an addition reaction with D-ribonolactone (2) is performed, the target C-nucleoside compound (3) can be obtained in 25% yield. However, the synthetic method has low yield and high production cost, which restricts the follow-up clinical research and application of the drug (WO2011035250A1).

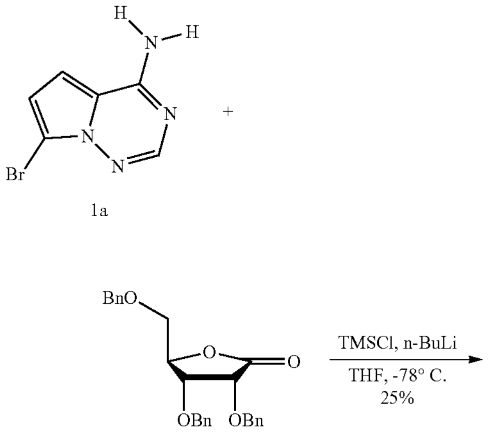

1a 2

-continued

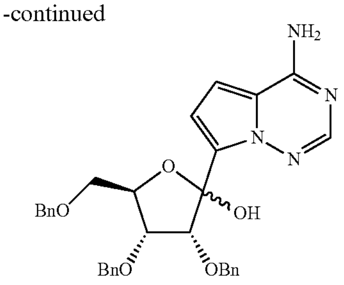

3

WO 2011035250

In view of the low yield of the above synthetic method, Sina Bavari et al. subsequently improved the addition reaction of this step (Nature, 2016, 531, 381-385). In the improved method, 7-iodopyrrolo[2,1-f][1,2,4]triazin-4-amine (1b) instead of 7-bromopyrrolo[2,1-f][1,2,4]triazin-4-amine (1a) is used, and Grignard reagents PhMgCl and i-PrMgCl·LiCl are used to complete the temporary silicon protection of the amino group in Compound 1b, then the metal-halogen exchange is carried out, the resultant heterocyclic metal compound is further subjected to an addition reaction with D-ribonolactone (2), which can increase the reaction yield to 40%. However, this reaction needs to temporarily protect the amino group in Compound 1b with TMSCl through phenyl Grignard reagent at 0° C., and then the temperature is lowered down to −20° C. and then the addition reaction with D-ribonolactone (2) is performed under the action of isopropyl Grignard reagent. This synthesis strategy requires frequent changes of reaction temperature during the feeding and reaction process, and usage of different Grignard reagents, and the operation is cumbersome.

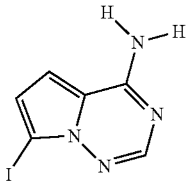

+

1b

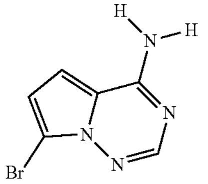

+

1a

-continued

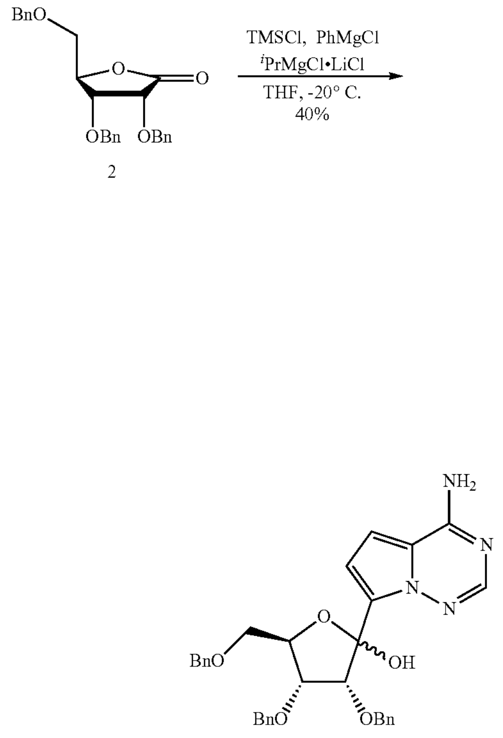

Nature, 2016, 531, 381-385

In addition to the above-mentioned addition methods using TMSCl as a temporary protecting group, the literature also discloses an addition method using 1,2-bis(chlorodimethylsilyl)ethane instead of TMSCl to temporarily protect the amino group in Compound 1 (Bioorg. Med. Chem. Lett. 2012, 22, 2705-2707; WO2014042433A2, WO2014035140A2). These methods need to complete the protection of amino group in Compound 1 and the addition reaction by using more than two metal reagents or at different temperatures, not only the yield is still not ideal (40% to 60%), but also the operation is cumbersome, which is not conducive to scale-up synthesis.

-continued

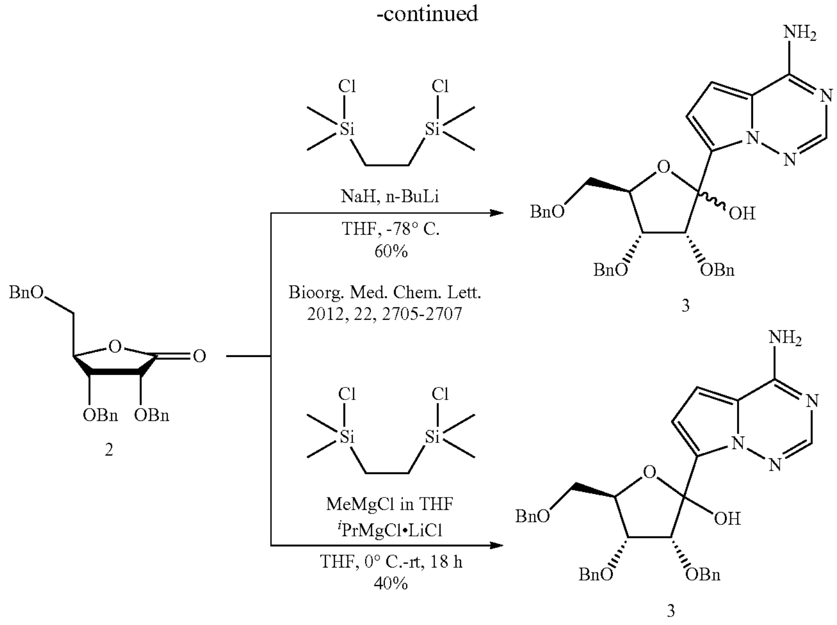

2 3 3

WO2014042433A2,
WO2014035140A2

In view of the problems of low yield, cumbersome operation, high cost, and difficulty in scale-up production of remdesivir reported in the existing reports, it is extremely important to develop a more concise and efficient synthetic method to prepare its chiral synthetic intermediate C-nucleoside compound (3), and the newly developed method should help to reduce the cost of drug production, thereby solving the problem of drug accessibility and satisfying the clinical application of remdesivir against SARS-CoV-2 virus infection.

CONTENTS OF THE INVENTION

The purpose of the present application is to provide a method for efficiently preparing a chiral C-nucleoside compound; another purpose of the present application is to provide a simple method for preparing a chiral C-nucleoside compound; another purpose of the present application is to provide a method for preparing a chiral C-nucleoside compound that is easy to implement and scale up; and another purpose of the present application is to provide a method for preparing a chiral C-nucleoside compound that can be produced on a large scale.

The purposes of the present application are achieved through the following technical solutions:

A method for preparing a C-nucleoside compound represented by Formula III or salt thereof, comprising:

a) providing a compound represented by Formula II;

b) in a solvent, in the presence of a secondary amine represented by Formula 4, a metal lithium reagent and 1,2-bis(chlorodimethylsilyl)ethane, allowing a compound represented by Formula 1 to react with the compound represented by Formula II to generate the C-nucleoside compound represented by Formula III,

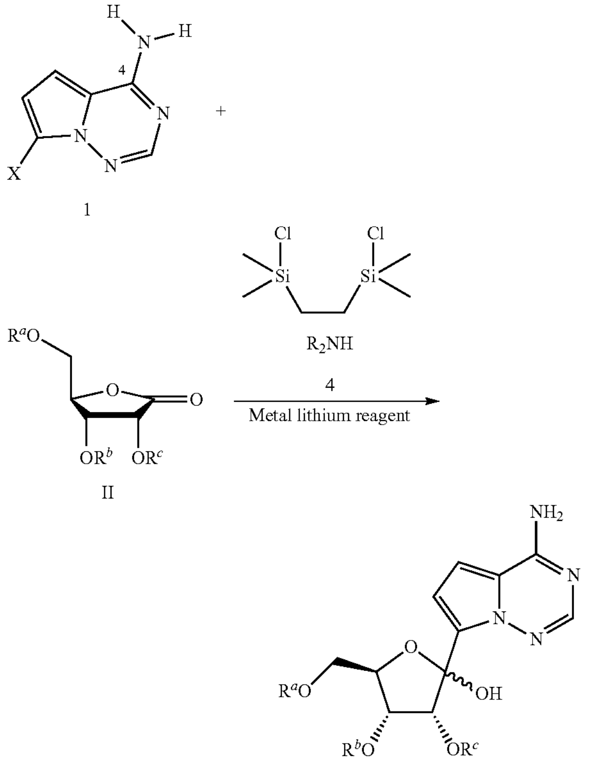

1 + II III in the compound represented by Formula 1, X is halogen; in the secondary amine represented by Formula 4, each R is independently $C_1$-$C_6$ alkyl, $C_3$-$C_6$ cycloalkyl or trimethylsilyl, or two Rs and the nitrogen atom to which they are attached together form a substituted or unsubstituted piperidine or pyrrolidine (e.g., 2,2,6,6-tetramethylpiperidine); in the compound represented by Formula II or Formula III, $R^a$, $R^b$ and $R^c$ are each independently methyl, benzyl (Bn), p-methoxybenzyl (PBM), trityl (Tr), tert-butyl or allyl;

in the compound represented by the Formula III, "~" indicates that the structural formula can represent the α configuration or the β configuration of the compound, or a mixture of the α configuration and the β configuration in any ratio.

In some embodiments, X in the compound of Formula 1 is a bromine atom or an iodine atom.

In some embodiments, X in the compound of Formula 1 is a bromine atom.

In some embodiments, X in the compound of Formula 1 is an iodine atom.

In some embodiments, each R in the secondary amine represented by Formula 4 is each independently methyl, ethyl, n-propyl, isopropyl, n-butyl, isobutyl, cyclopropyl, cyclobutyl, cyclopentyl, cyclohexyl or trimethylsilyl.

In some embodiments, each R in the secondary amine represented by Formula 4 is independently methyl.

In some embodiments, each R in the secondary amine represented by Formula 4 is independently ethyl.

In some embodiments, each R in the secondary amine represented by Formula 4 is independently n-propyl.

In some embodiments, each R in the secondary amine represented by Formula 4 is independently isopropyl.

In some embodiments, each R in the secondary amine represented by Formula 4 is independently n-butyl.

In some embodiments, each R in the secondary amine represented by Formula 4 is independently isobutyl.

In some embodiments, each R in the secondary amine represented by Formula 4 is independently cyclopropyl.

In some embodiments, each R in the secondary amine represented by Formula 4 is independently cyclobutyl.

In some embodiments, each R in the secondary amine represented by Formula 4 is each independently cyclopentyl.

In some embodiments, each R in the secondary amine represented by Formula 4 is independently cyclohexyl.

In some embodiments, each R in the secondary amine represented by Formula 4 is independently trimethylsilyl.

In some embodiments, the two Rs in the secondary amine represented by Formula 4 and the nitrogen atom to which they are attached together form piperidine, pyrrolidine, or 2,2,6,6-tetramethylpiperidine.

In some embodiments, the two Rs in the secondary amine represented by Formula 4 and the nitrogen atom to which they are attached together form piperidine.

In some embodiments, the two Rs in the secondary amine represented by Formula 4 and the nitrogen atom to which they are attached together form pyrrolidine.

In some embodiments, the two Rs in the secondary amine represented by Formula 4 and the nitrogen atom to which they are attached together form 2,2,6,6-tetramethylpiperidine.

In some embodiments, the secondary amine represented by Formula 4 is diethylamine, dipropylamine, diisopropylamine, dibutylamine, diisobutylamine, dicyclohexylamine, dicyclopentylamine, dicyclopropylamine, 2,2,6,6-tetramethylpiperidine or hexamethyldisilazane.

In some embodiments, the secondary amine represented by Formula 4 is diethylamine, dipropylamine, diisopropylamine, dibutylamine, diisobutylamine, dicyclohexylamine, 2,2,6,6-tetramethylpiperidine or hexamethyldisilazane.

In some embodiments, the secondary amine represented by Formula 4 is diisopropylamine, diisobutylamine, dicyclohexylamine, 2,2,6,6-tetramethylpiperidine or hexamethyldisilazane.

In some embodiments, the secondary amine represented by Formula 4 is diisopropylamine, diisobutylamine, dicyclohexylamine, or 2,2,6,6-tetramethylpiperidine.

In some embodiments, the secondary amine represented by Formula 4 is hexamethyldisilazane.

In some embodiments, the secondary amine represented by Formula 4 is diisopropylamine.

In some embodiments, the secondary amine represented by Formula 4 is diisobutylamine.

In some embodiments, the secondary amine represented by Formula 4 is dicyclohexylamine.

In some embodiments, the secondary amine of Formula 4 is 2,2,6,6-tetramethylpiperidine.

In some embodiments, the secondary amine represented by Formula 4 is diethylamine, dipropylamine, or dibutylamine.

In some embodiments, the secondary amine represented by Formula 4 is diethylamine.

In some embodiments, the secondary amine represented by Formula 4 is dipropylamine.

In some embodiments, the secondary amine represented by Formula 4 is dibutylamine.

In some embodiments, $R^a$, $R^b$, and $R^c$ in the compound represented by Formula II or Formula III is each independently benzyl (Bn).

In some embodiments, $R^a$, $R^b$, and $R^c$ in the compound represented by Formula II or Formula III is each independently p-methoxybenzyl (PBM).

In some embodiments, $R^a$, $R^b$, and $R^c$ in the compound represented by Formula II is each independently benzyl (Bn).

In some embodiments, $R^a$, $R^b$, and $R^c$ in the compound represented by Formula III is each independently benzyl (Bn).

In some embodiments, the solvent of the present application is an organic solvent such as tetrahydrofuran.

In some embodiments, the metal lithium reagent of the present application is methyllithium, n-butyllithium, tert-butyllithium, lithium diisopropylamide, lithium bis(trimethylsilyl)amide, lithium bis(trifluoromethanesulfonimide), lithium triethylborohydride, lithium borohydride, lithium amide or lithium hydride.

In some embodiments, the metal lithium reagent of the present application is n-butyllithium.

In some embodiments, in the method for preparing C-nucleoside compound as described in the present application, the step b) comprises:

b1) dissolving the compound represented by Formula 1 and 1,2-bis(chlorodimethylsilyl)ethane in the solvent, and adding the secondary amine represented by Formula 4 to obtain a mixture;

b2) sequentially adding the metal lithium reagent and the compound represented by Formula II to the mixture obtained in b1), and allowing the compound represented by Formula 1 to react with the compound represented by Formula II to obtain the compound represented by Formula III.

In some embodiments, in the method for preparing C-nucleoside compound as described in the present application, step b) is performed under anhydrous and anaerobic conditions.

In some embodiments, in the method for preparing C-nucleoside compound as described in the present application, the metal lithium reagent and the compound represented by Formula II are sequentially added to the mixture obtained in b1) at a temperature of 0° C. to −80° C. (e.g., 0° C. to −78° C., preferably −78° C.).

In some embodiments, in the method for preparing C-nucleoside compound as described in the present application, the metal lithium reagent and the compound represented by Formula II are sequentially added to the mixture obtained in b1) at a temperature of −70° C. to −80° C.

In some embodiments, in the method for preparing C-nucleoside compound as described in the present application, the metal lithium reagent and the compound represented by Formula II are sequentially added to the mixture obtained in b1) at a temperature of −78° C. to −80° C.

In some embodiments, in the method for preparing C-nucleoside compound as described in the present application, the compound represented by Formula 1 is reacted with the compound represented by Formula II, and the initial concentration of the compound represented by Formula 1 is 0.06 to 0.3 mol/L, such as 0.08 mol/L, 0.1 mol/L, 0.15 mol/L, 0.18 mol/L, 0.2 mol/L, 0.25 mol/L.

In some embodiments, in the method for preparing C-nucleoside compound as described in the present application, the compound represented by Formula 1 is reacted with the compound represented by Formula II, and the initial concentration of the compound represented by Formula 1 is 0.08 to 0.25 mol/L.

In some embodiments, in the method for preparing C-nucleoside compound as described in the present application, the compound represented by Formula 1 is reacted with the compound represented by Formula II at a temperature of 0° C. to −80° C. (e.g., 0° C. to −78° C., preferably −78° C.).

In some embodiments, in the method for preparing C-nucleoside compound as described in the present application, the compound represented by Formula 1 is reacted with the compound represented by Formula II at a temperature of −70° C. to −80° C.

In some embodiments, in the method for preparing C-nucleoside compound as described in the present application, the compound represented by Formula 1 is reacted with the compound represented by Formula II at a temperature of −78° C. to −80° C.

In some embodiments, in the method for preparing C-nucleoside compound as described in the present application, the feeding molar ratio of the compound represented by Formula 1 to the compound represented by Formula II is 1:1.5~3, such as about 1:1.6, about 1:1.8, about 1:2.

In some embodiments, in the method for preparing C-nucleoside compound as described in the present application, the feeding molar ratio of the compound represented by Formula 1 to the compound represented by Formula II is 1:1.6~3.

In some embodiments, in the method for preparing C-nucleoside compound as described in the present application, the feeding molar ratio of the compound represented by Formula 1 to the compound represented by Formula II is 1:1.8~3.

In some embodiments, in the method for preparing C-nucleoside compound as described in the present application, the feeding molar ratio of the compound represented by Formula 1 to the compound represented by Formula II is 1:1.9~3.

In some embodiments, in the method for preparing C-nucleoside compound as described in the present application, the feeding molar ratio of the compound represented by Formula 1 to the compound represented by Formula II is 1:2~3.

In some embodiments, in the method for preparing C-nucleoside compound as described in the present application, the feeding molar ratio of the compound represented by Formula 1 to the compound represented by Formula II is 1:1.6~2.5.

In some embodiments, in the method for preparing C-nucleoside compound as described in the present application, the feeding molar ratio of the compound represented by Formula 1 to the compound represented by Formula II is 1:1.8~2.5.

In some embodiments, in the method for preparing C-nucleoside compound as described in the present application, the feeding molar ratio of the compound represented by Formula 1 to the compound represented by Formula II is 1:1.9~2.5.

In some embodiments, in the method for preparing C-nucleoside compound as described in the present application, the feeding molar ratio of the compound represented by Formula 1 to the compound represented by Formula II is 1:2~2.5.

In some embodiments, in the method for preparing C-nucleoside compound as described in the present application, the compound represented by Formula 1 is reacted with the compound represented by Formula II, the initial concentration of the compound represented by Formula 1 is 0.06 to 0.3 mol/L, and the feeding molar ratio of the compound represented by Formula 1 to the compound represented by Formula II is 1:1.5~3.

In some embodiments, in the method for preparing C-nucleoside compound as described in the present application, the compound represented by Formula 1 is reacted with the compound represented by Formula II, the initial concentration of the compound represented by Formula 1 is 0.06 to 0.3 mol/L, and the feeding molar ratio of the compound represented by Formula 1 to the compound represented by Formula II is 1:1.6~3.

In some embodiments, in the method for preparing C-nucleoside compound as described in the present application, the compound represented by Formula 1 is reacted with the compound represented by Formula II, the initial concentration of the compound represented by Formula 1 is 0.06 to 0.3 mol/L, and the feeding molar ratio of the compound represented by Formula 1 to the compound represented by Formula II is 1:1.8~3.

In some embodiments, in the method for preparing C-nucleoside compound as described in the present application, the compound represented by Formula 1 is reacted with the compound represented by Formula II, the initial concentration of the compound represented by Formula 1 is 0.06 to 0.3 mol/L, and the feeding molar ratio of the compound represented by Formula 1 to the compound represented by Formula II is 1:1.9~3.

In some embodiments, in the method for preparing C-nucleoside compound as described in the present application, the compound represented by Formula 1 is reacted with the compound represented by Formula II, the initial concentration of the compound represented by Formula 1 is 0.06 to 0.3 mol/L, and the feeding molar ratio of the compound represented by Formula 1 to the compound represented by Formula II is 1:2~3.

In some embodiments, in the method for preparing C-nucleoside compound as described in the present application, the compound represented by Formula 1 is reacted with the compound represented by Formula II, the initial concentration of the compound represented by Formula 1 is 0.08 to 0.25 mol/L, and the feeding molar ratio of the compound represented by Formula 1 to the compound represented by Formula II is 1:1.6~2.

In some embodiments, in the method for preparing C-nucleoside compound as described in the present application, the compound represented by Formula 1 is reacted with the compound represented by Formula II, the initial concentration of the compound represented by Formula 1 is 0.08 to 0.25 mol/L, and the feeding molar ratio of the compound represented by Formula 1 to the compound represented by Formula II is 1:1.8~2.

In some embodiments, in the method for preparing C-nucleoside compound as described in the present application, the compound represented by Formula 1 is reacted with the compound represented by Formula II, the initial concentration of the compound represented by Formula 1 is 0.08 to 0.25 mol/L, and the feeding molar ratio of the compound represented by Formula 1 to the compound represented by Formula II is 1:1.9~2.

In some embodiments, in the method for preparing C-nucleoside compound as described in the present application, the compound represented by Formula 1 is reacted with the compound represented by Formula II, the initial concentration of the compound represented by Formula 1 is 0.08 to 0.25 mol/L, and the feeding molar ratio of the compound represented by Formula 1 to the compound represented by Formula II is 1:2~2.5.

In some embodiments, in the method for preparing C-nucleoside compound as described in the present application, the feeding molar ratio of the compound represented by Formula 1 to the metal lithium reagent is 1:3.5~4.5, for example, about 1:4.

In some embodiments, in the method for preparing C-nucleoside compound as described in the present application, the feeding molar ratio of the compound represented by Formula 1 to 1,2-bis(chlorodimethylsilyl)ethane is 1:1~1.5, for example, about 1:1.1, about 1:1.2, about 1:1.3, about 1:1.4.

In some embodiments, in the method for preparing C-nucleoside compound as described in the present application, the feeding molar ratio of the compound represented by Formula 1 to the secondary amine represented by Formula 4 is 1: 1-1.5, for example, about 1:1.1, about 1:1.2, about 1:1.3, about 1:1.4.

In some embodiments, in the method for preparing C-nucleoside compound as described in the present application, the reaction of the compound represented by Formula 1 and the compound represented by Formula II comprises:

under the action of the secondary amine represented by Formula 4 and the metal lithium reagent, allowing the 4-position amino group in the compound represented by Formula 1 to undergo a bis-silicon protection by using 1,2-bis(chlorodimethylsilyl)ethane to generate a compound represented by Formula 5;

5

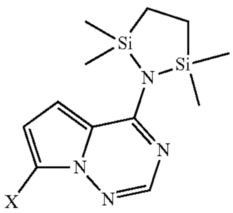

-continued

6

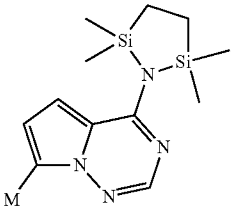

under the action of the secondary amine represented by Formula 4 and the metal lithium reagent, the compound represented by Formula 5 undergoing a lithium-halogen exchange to obtain a compound represented by the intermediate Formula 6, wherein M is Li;

the compound represented by Formula 6 undergoing an addition reaction with the compound represented by Formula II to generate the C-nucleoside compound represented by the Formula III.

In some embodiments, the synthetic scheme of the method for preparing C-nucleoside compound as described in the present application is:

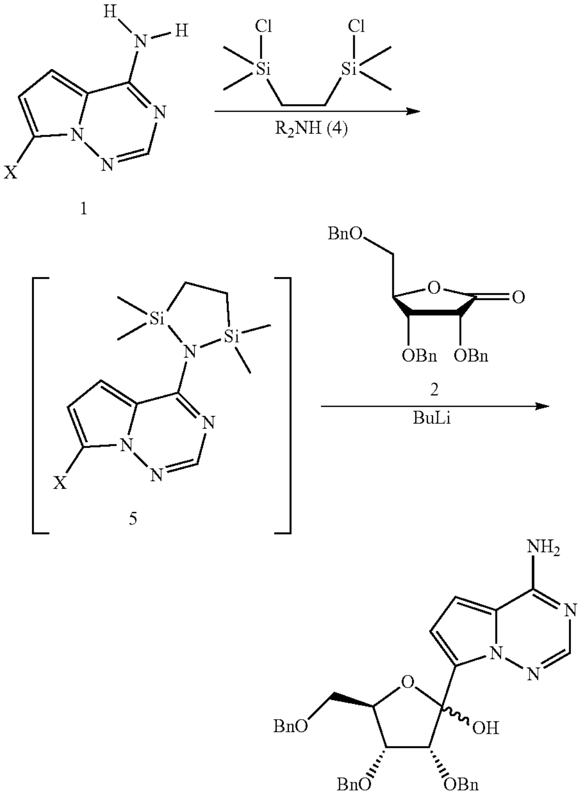

3

The specific steps of this technical scheme are as follows: the heterocyclic Compound 1 are sequentially mixed with 1,2-bis(chlorodimethylsilyl)ethane, amine 4 and butyllithium, and undergoes an addition reaction with ribonolactone 2 at the same reaction temperature to complete the synthesis of nucleoside Compound 3. In the above technical scheme, the temporary bis-silicon protection (Compound 5) of the 4-position amine group in Compound 1 is firstly achieved with 1,2-bis(chlorodimethylsilyl)ethane under the action of amine 4 and butyllithium, then under the combined action of amine 4 and butyllithium, intermediate 5 undergoes a lithium-halogen exchange, and the obtained heterocyclic lithium intermediate undergoes an addition reaction with ribonolactone 2 to achieve the preparation of C-nucleoside Compound 3.

The present application also provides a method for preparing a C-nucleoside compound, comprising:

1) in a solvent, under the action of a secondary amine represented by Formula 4 and a metal lithium reagent, allowing the 4-position amino group in the compound represented by Formula 1 to undergo a bis-silicon protection by using 1,2-bis(chlorodimethylsilyl)ethane to generate a compound represented by a intermediate Formula 5;

1

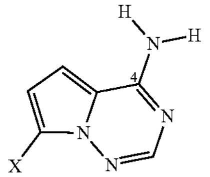

II

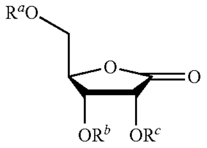

4

$R_2NH$

5

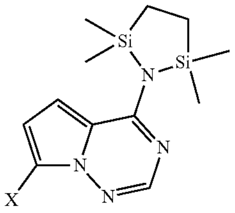

6

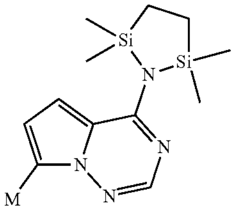

III

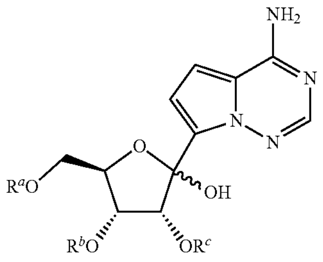

2) under the action of the secondary amine represented by Formula 4 and the metal lithium reagent, the compound represented by Formula 5 undergoing a lithium-halogen exchange to generate a compound represented by a intermediate Formula 6, wherein M is Li;

3) the compound represented by Formula 6 undergoing an addition reaction with a compound represented by Formula II to generate a C-nucleoside compound represented by Formula III, wherein, the definitions of the solvent, X, R, $R^a$, $R^b$, $R^c$, , as well as the reaction conditions, feeding ratios and so on are as described in the present application.

Definition

Unless otherwise defined below, all technical and scientific terms used herein are intended to have the same meanings as commonly understood by one skilled in the art. References to techniques used herein are intended to refer to techniques commonly understood in the art, including those variations or substitutions of equivalent techniques that would be obvious to one skilled in the art. While the following terms are believed to be well understood by one skilled in the art, the following definitions are set forth to better explain the present application.

As used herein, the terms "comprising", "including", "having", "containing" or "involving" and other variations thereof herein are inclusive or open-ended and do not exclude other unenumerated elements or method steps.

As used herein, the term "alkyl" is defined as a straight or branched chain saturated aliphatic hydrocarbon group. In some embodiments, the alkyl has 1 to 6, for example, 1 to 4, carbon atoms. For example, as used herein, the term "$C_1$-$C_6$ alkyl" refers to a straight or branched chain group having 1 to 6 carbon atoms, such as methyl, ethyl, n-propyl, isopropyl, n-butyl, isobutyl, sec-butyl, tert-butyl, n-pentyl or n-hexyl.

As used herein, the term "$C_3$-$C_6$ cycloalkyl" refers to a saturated or unsaturated non-aromatic monocyclic or polycyclic (e.g., bicyclic) hydrocarbon ring having 3 to 6 ring carbon atoms, for example, cyclopropyl, cyclobutyl, cyclopentyl, cyclohexyl, which may be optionally substituted with one or more (e.g., 1, 2, or 3) suitable substituents, for example, methyl-substituted cyclopropyl, methyl-substituted cyclohexyl.

As used herein, the term "halogen" group is defined to include F, Cl, Br or I.

As used herein, the term "about" should be understood as a value which is within the range of 10%, 9%±, 8%±, 7%, 6%, 5%, 4%, 3%, 2%±, %, 0.5%, 0.1%, 0.05% or 0.01% of the designated value.

The beneficial effects of the present application are as follows:

The method for preparing a chiral intermediate C-nucleoside compound of remdesivir provided by the present application has one or more of the following advantages:

1) this method has a high reaction yield, for example, the yield is not less than 40%, preferably not less than 45%, and more preferably not less than 70%;
2) the method is simple to operate;
3) this method uses a single metal reagent;
4) the temperature conditions of the reaction of this method are stable, and the operation process does not need to frequently change the reaction system;
5) this method is suitable for scale-up synthesis and may be adapted to the large-scale production of remdesivir;
6) the method is used to prepare a chiral intermediate C-nucleoside compound of remdesivir, and the cost is low.

SPECIFIC MODELS FOR CARRYING OUT THE INVENTION

The technical solutions of the present application are described in further detail below, but the protection scope of the present application is not limited to the following description.

Example 1

Synthesis of Chiral C-Nucleoside Compound Represented by Formula 3

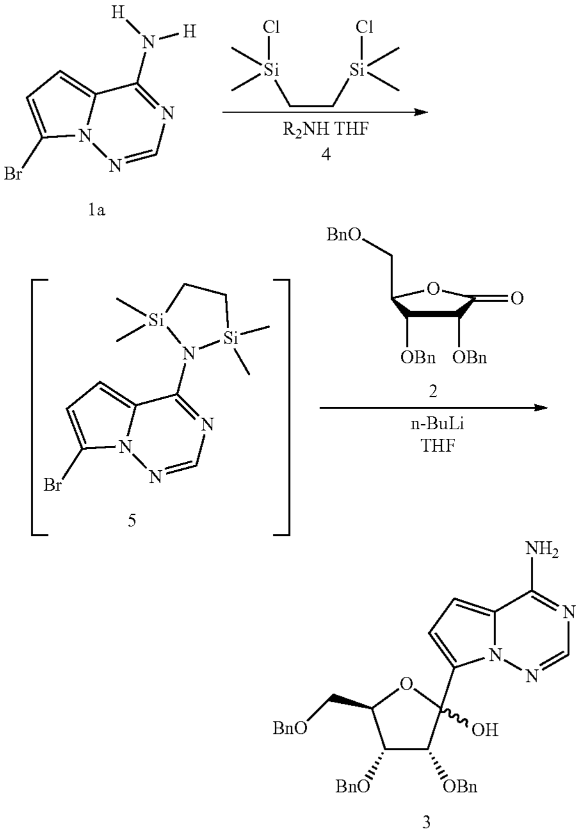

Under anhydrous and anaerobic conditions, Compound 1a (10.0 g, 46.94 mmol) and 1,2-bis(chlorodimethylsilyl)ethane (11.1 g, 51.63 mmol) were dissolved in THF (100 mL), then diisopropylamine represented by Formula 4 (7.3 mL, 51.63 mmol) was added. N-butyllithium (81 mL, 201.8 mmol) and ribonolactone (39.3 g, 93.88 mmol) represented by Formula 2 in THF solution (50 mL) were sequentially added to the reaction solution at −78° C. The reaction solution reacted at −78° C. for 2 hours, then citric acid in aqueous solution (1M, 200 mL) was added to quench the reaction, the reaction solution was warmed to room temperature, and the aqueous layer was extracted with ethyl acetate (3×200 mL), and the organic layers were combined, washed sequentially with water (1×250 mL), saturated $NaHCO_3$ solution (1×250 mL), and saturated NaCl solution (1×250 mL). The organic layer was dried with anhydrous magnesium sulfate, and filtered, and the solvent was removed under reduced pressure, and the obtained crude product was separated and purified by silica gel column chromatography (developing solvent: firstly gradient eluted with petroleum ether:ethyl acetate=1:1 to pure ethyl acetate, then eluted with methanol/ethyl acetate=10%) to obtain a white foamy solid compound (19.2 g), which was the chiral C-nucleoside compound represented by Formula 3, with a yield of 74%. $^1$H-NMR (400 MHz, DMSO-d6): δ 8.06 (br s, 2H), 7.99 (s, 1H), 7.37-7.22 (m, 11H), 7.19-7.10 (m, 3H), 7.03-6.97 (m, 2H), 6.95 (d, J=4.8 Hz, 1H), 5.39 (d, J=5.9 Hz, 1H), 5.05 (d, J=5.2 Hz, 1H), 4.61-4.54 (m, 2H), 4.52-4.42 (m, 4H), 4.06-3.98 (m, 1H), 3.93 (dd, J=5.9, 4.4 Hz, 1H), 3.69 (dd, J=10.1, 3.4 Hz, 1H), 3.47 (dd, J=10.0, 6.4 Hz, 1H); 13C-NMR (100 MHz, DMSO-d6): δ 187.98, 155.88, 148.96, 138.63, 138.43, 138.14, 128.67, 128.14, 128.12, 127.82, 127.54, 127.44, 127.26, 127.21, 127.09, 118.60, 117.51, 103.15, 102.30, 81.91, 80.92, 72.50, 72.33, 71.74, 71.44, 69.42; HRMS calcd for $C_{32}H_{32}N_4O_5$ 552.2373, found 552.2362.

Example 2

According to the method described in Example 1, Compound 1a and the ribonolactone represented by Formula 2 were used as substrates, the yields of synthesis of the chiral C-nucleoside compound represented by Formula 3 under the action of different secondary amines represented by Formula 4 were compared, and the data obtained were shown in the table below.

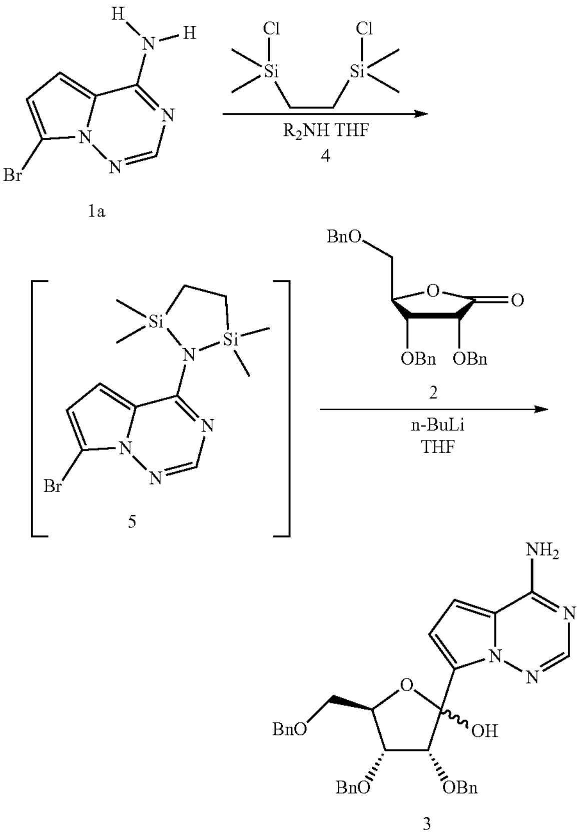

| Item | Amine (4) | Product 3 (yield) |
|---|---|---|
| 1 | 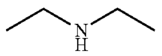 | 41% |

-continued

| Item | Amine (4) | Product 3 (yield) |
|---|---|---|
| 2 | 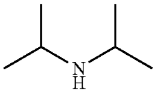 | 74% |
| 3 | 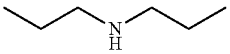 | 45% |
| 4 | 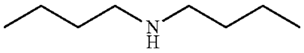 | 54% |
| 5 | 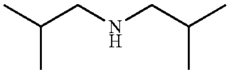 | 71% |
| 6 | 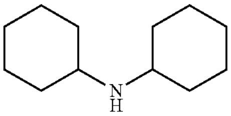 [SMILES: C1CCC(NC2CCCCC2)CC1] | 70% |
| 7 | 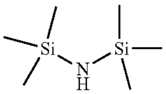 | 57% |
| 8 | 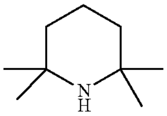 | 74% |

Example 3

According to the method described in Example 1, Compound 1a was reacted on a scale of 10 grams, other reaction conditions remained unchanged, and only the concentration of Compound 1a in the reaction solution and the equivalent number of ribonolactone represented by Formula 2 were changed, the obtained data of synthesis yields of the chiral C-nucleoside compounds represented by Formula 3 were shown in the table below.

| No. | Compound 2 (equivalent) | Concentration of Compuond 1a (mol/L) | Product 3 (yield) |
|---|---|---|---|
| 1 | 2.0 | 0.08 | 75% |
| 2 | 2.0 | 0.20 | 74% |
| 3 | 2.0 | 0.25 | 70% |
| 4 | 1.8 | 0.20 | 62% |
| 5 | 1.6 | 0.20 | 59% |

Example 4

According to the method described in Example 1, Compound 1a and Compound 1b were used as substrates, respectively, and other reaction conditions unchanged, 1 equivalent of Compound 1 was subjected to an addition reaction with 2.5 equivalents of ribonolactone represented by Formula 2, and the reaction was carried out in the presence of different amines or bases. The synthesis yield data of the chiral C-nucleoside compound represented by the Formula 3 obtained under the conditions of different amine or base were shown in the following table.

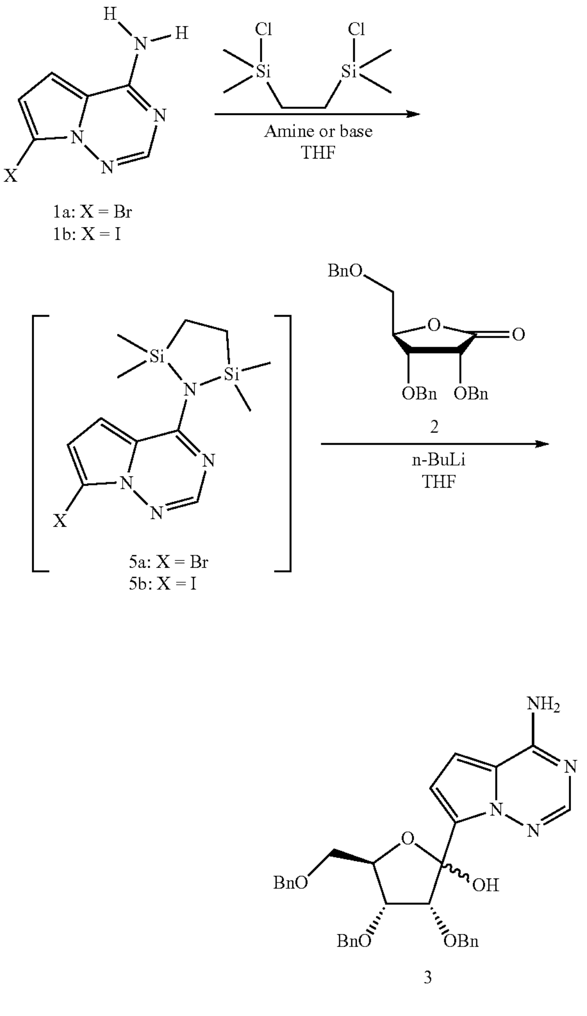

| No. | Compound 1 | Amine or base (equivalent) | n-BuLi (equivalent) | Reaction temperature | Product 3 (yield) |
|---|---|---|---|---|---|
| 1 | 1a | i-$Pr_2NH$ (1.1) | 4.3 | −78° C. | 74% |
| 2 | 1a | NaH (2.5) | 3.3 | Room temperature/−78° C. | 42% |
| 3 | 1b | i-$Pr_2NH$ (1.1) | 4.3 | −78° C. | 59% |
| 4 | 1b | No amine added i-$Pr_2NH$ | 3.3 | −78° C. | 24% |

The above are only preferred embodiments of the present application, and it should be understood that the present application is not limited to the form disclosed herein, and they should not be regarded as an exclusion of other embodiments, but may be used in various other combinations, modifications and environments, and can be modified within the scope of the concepts described herein according to the above teachings or skill or knowledge in the relevant field. However, the modifications and changes made by one skilled in the art do not depart from the spirit and scope of the present application, and should be within the scope of protection of the appended claims of the present application.

What is claimed is:

1. A method for preparing a C-nucleoside compound represented by Formula III or salt thereof, comprising:

a) providing a compound represented by Formula II;

b) in a solvent, in the presence of a secondary amine represented by Formula 4, a metal lithium reagent and 1,2-bis(chlorodimethylsilyl) ethane, allowing a compound represented by Formula 1 to react with the compound represented by Formula II to generate the C-nucleoside compound represented by Formula III,

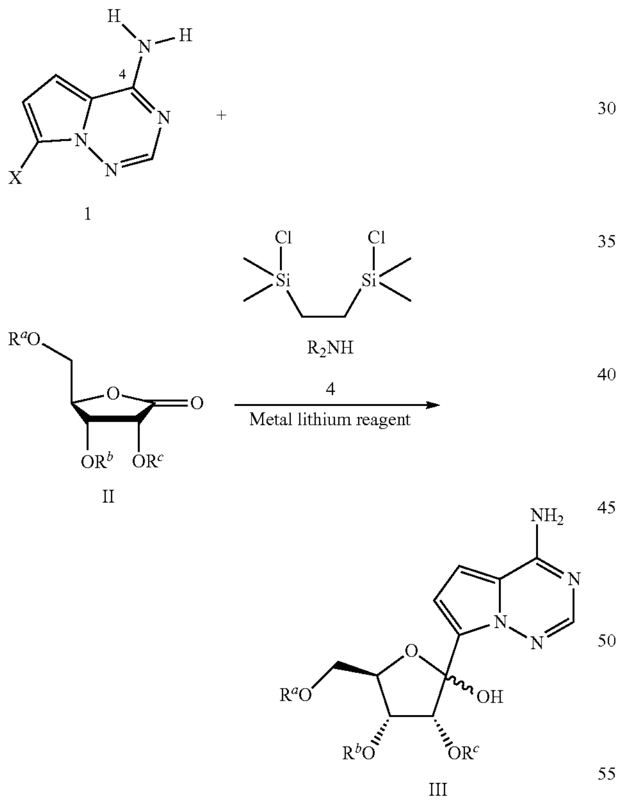

1 II III in the compound represented by Formula 1, X is halogen;

in the secondary amine represented by Formula 4, each R is independently isopropyl, isobutyl or cyclohexyl, or two Rs together with the nitrogen atom to which they are attached form a 2,2,6,6-tetramethylpiperidine;

in the compound represented by Formula II or Formula III, $R^a$, $R^b$ and $R^c$ are each benzyl;

in the compound represented by the Formula III, "∿" indicates that the bond is in the α configuration or the β configuration, or a mixture thereof in any ratio.

2. The method for preparing the C-nucleoside compound according to claim 1, wherein X is bromine or iodine.

3. The method for preparing the C-nucleoside compound according to claim 2, wherein X is bromine.

4. The method for preparing the C-nucleoside compound according to claim 1, wherein the solvent is an organic solvent.

5. The method for preparing the C-nucleoside compound according to claim 4, wherein the solvent is tetrahydrofuran.

6. The method for preparing the C-nucleoside compound according to claim 1, wherein the metal lithium reagent is methyllithium, n-butyllithium, tert-butyllithium, lithium diisopropylamide, or lithium bis(trimethylsilyl)amide.

7. The method for preparing the C-nucleoside compound according to claim 6, wherein the metal lithium reagent is n-butyllithium.

8. The method for preparing the C-nucleoside compound according to claim 1, wherein step b) comprises:

b1) dissolving the compound represented by Formula 1 and 1,2-bis(chlorodimethylsilyl) ethane in the solvent, and adding the secondary amine represented by Formula 4 to obtain a mixture;

b2) sequentially adding the metal lithium reagent and the compound represented by Formula II to the mixture obtained in b1), and allowing the compound represented by Formula 1 to react with the compound represented by Formula II to obtain the compound represented by Formula III.

9. The method for preparing the C-nucleoside compound according to claim 1, wherein the compound represented by Formula 1 is reacted with the compound represented by Formula II, and the initial concentration of the compound represented by Formula 1 is 0.06 to 0.3 mol/L.

10. The method for preparing the C-nucleoside compound according to claim 1, wherein the compound represented by Formula 1 is reacted with the compound represented by Formula II at a temperature of 0° C. to −80° C.

11. The method for preparing the C-nucleoside compound according to claim 1, wherein the feeding molar ratio of the compound represented by Formula 1 to the compound represented by Formula II is 1:1.5~3.

12. The method for preparing the C-nucleoside compound according to claim 1, wherein step b) is carried out under anhydrous and anaerobic conditions.

13. The method for preparing the C-nucleoside compound according to claim 1, wherein the reaction between the compound represented by Formula 1 and the compound represented by Formula II comprises:

under the action of the secondary amine represented by Formula 4 and the metal lithium reagent, allowing the 4-position amino group in the compound represented by Formula 1 to undergo a bis-silicon protection by using 1,2-bis(chlorodimethylsilyl) ethane to generate a compound represented by the intermediate Formula 5;

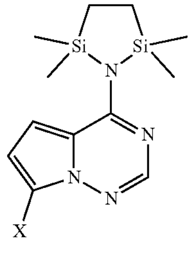

5

-continued

6

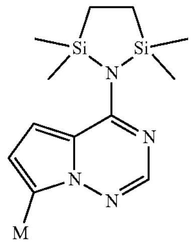

under the action of the secondary amine represented by Formula 4 and the metal lithium reagent, the compound represented by Formula 5 undergoing a lithium-halogen exchange to generate a compound represented by the intermediate Formula 6, wherein M is Li;

the compound represented by the Formula 6 undergoing an addition reaction with the compound represented by the Formula II to generate the C-nucleoside compound represented by the Formula III.

14. The method for preparing the C-nucleoside compound according to claim 1, wherein the secondary amine represented by Formula 4 is diisopropylamine, diisobutylamine, dicyclohexylamine, or 2,2,6,6-tetramethylpiperidine.

15. The method for preparing the C-nucleoside compound according to claim 1, wherein the feeding molar ratio of the compound represented by Formula 1 to the lithium metal reagent is 1:3.5~4.5.

16. The method for preparing the C-nucleoside compound according to claim 1, wherein the feeding molar ratio of the compound represented by Formula 1 to 1,2-bis(chlorodimethylsilyl) ethane is 1:1~1.5.

17. The method for preparing the C-nucleoside compound according to claim 1, wherein the feeding molar ratio of the compound represented by Formula 1 to the secondary amine represented by Formula 4 is 1:1~1.5.

18. A method for preparing a C-nucleoside compound, comprising:

1) In a solvent, under the action of a secondary amine represented by Formula 4 and a metal lithium reagent, allowing the 4-position amino group in the compound represented by Formula 1 to undergo a bis-silicon protection by using 1,2-bis(chlorodimethylsilyl) ethane to generate a compound represented by the intermediate Formula 5;

1

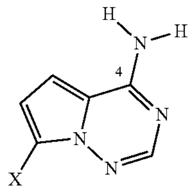

-continued

II

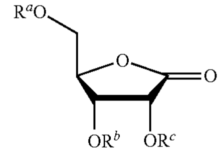

4

$R_2NH$

5

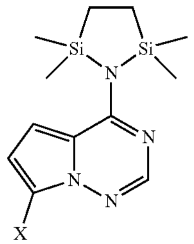

6

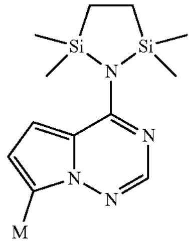

III

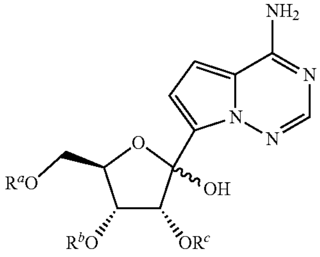

2) Under the action of the secondary amine represented by Formula 4 and the metal lithium reagent, the compound represented by Formula 5 undergoing lithium-halogen exchange to generate a compound represented by the intermediate Formula 6, wherein M is Li;

3) the compound represented by Formula 6 undergoing an addition reaction with a compound represented by Formula II to generate a C-nucleoside compound represented by Formula III, wherein, in the compound represented by Formula 1, X is halogen;

in the secondary amine represented by Formula 4, each R is independently isopropyl, isobutyl or cyclohexyl, or two Rs together with the nitrogen atom to which they are attached form a 2,2,6,6-tetramethylpiperidine;

in the compound represented by Formula II or Formula III, $R^a$, $R^b$ and $R^c$ are each benzyl;

in the compound represented by the Formula III, "∿" indicates that the bond is in the α configuration or the β configuration, or a mixture thereof in any ratio.

* * * * *